United States Patent [19]

Yamamoto

[11] Patent Number: 5,102,661
[45] Date of Patent: * Apr. 7, 1992

[54] 2-ETHOXYMETHYL-5-HYDROXY-GAMMA-PYRONE AND MELANOGENESIS-INHIBITING ENDERMIC PREPARATION CONTAINING THE SAME AS ACTIVE INGREDIENT

[75] Inventor: Shinji Yamamoto, Fukuoka, Japan

[73] Assignee: Sansho Seiyaku Co., Ltd., Fukuoka, Japan

[*] Notice: The portion of the term of this patent subsequent to Nov. 5, 2008 has been disclaimed.

[21] Appl. No.: 577,943

[22] Filed: Sep. 5, 1990

[30] Foreign Application Priority Data

Sep. 14, 1989 [JP] Japan .................................. 1-239643

[51] Int. Cl.$^5$ .............................................. A61K 7/00
[52] U.S. Cl. ..................................... 424/401; 424/59; 424/62; 514/460; 514/844
[58] Field of Search .................. 424/401, 62; 514/460

[56] References Cited

U.S. PATENT DOCUMENTS

| | | | |
|---|---|---|---|
| 4,545,982 | 10/1985 | Takahashi | 514/784 |
| 4,696,813 | 9/1987 | Higa | 424/62 |
| 4,847,074 | 7/1989 | Hatae | 424/62 |

OTHER PUBLICATIONS

The Merck Index, 1983, 10th Ed. p. 764 ref. no., 5153.

*Primary Examiner*—Thurman K. Page
*Assistant Examiner*—James M. Spear
*Attorney, Agent, or Firm*—Jordan and Hamburg

[57] ABSTRACT

The compound 2-ethoxymethyl-5-hydroxy-γ-pyrone and a melanogenesis-inhibiting endermic preparation for external application containing the compound as an active ingredient. The endermic preparations are almost non-toxic and have an extremely high melanogenesis-inhibiting activity.

6 Claims, 2 Drawing Sheets

2-ETHOXYMETHYL-5-HYDROXY-GAMMA-PYRONE AND MELANOGENESIS-INHIBITING ENDERMIC PREPARATION CONTAINING THE SAME AS ACTIVE INGREDIENT

BACKGROUND OF THE INVENTION

The present invention relates to a new compound, 2-ethoxymethyl-5-hydroxy-γ-pyrone, and a melanogenesis-inhibiting endermic preparation for external application which contains the same new compound as an active ingredient and which is effective for curing and preventing pigmentation diseases such as chloasma, senile moles, sunlight-induced moles or pigmented spots after inflammation and for whitening human skin.

In order to remove freckles, spots or the like as appear on the skin, a cosmetic material containing a peroxide such as hydrogen peroxide or zinc peroxide has been used for a long time.

However, since the peroxides are extremely unstable, they have some difficulties when stored and when incorporated into cosmetic bases. Additionally, they do not have a sufficient skin-whitening effect.

Further, cosmetic materials containing vitamin C, cysteine, colloidal sulfur or the like have been used for the purpose of skin-whitening, but the effect of the additives is not sufficiently satisfactory.

Recently, kojic acid has been found to be a substance having an excellent effect for inhibiting formation of melanin in human skin. Accordingly, there have been developed a kojic acid-containing whitening cosmetic material (JP-B-56-13569—the term "JP-B" as used herein means an "examined Japanese Patent Publication"), a skin-whitening cosmetic material containing an ester of kojic acid with an aromatic carboxylic acid such as cinnamic acid or benzoic acid (JP-B-60-10005), and a skin-whitening cosmetic material containing a monoester of kojic acid with an aliphatic carboxylic acid (JP-B-61-60801 and 60-7961).

As mentioned above, kojic acid and kojic acid esters are excellent substances for inhibiting formation of melanin. It is known that, when the substances are incorporated into cosmetic materials or endermic preparations for external application as a main component thereof and are applied to the skin, they display an excellent skin-whitening and melanogensis-inhibiting effect without injuring the skin. However, other substances having a higher melanogensis-inhibiting effect are greatly desired in this technical field.

SUMMARY OF THE INVENTION

The object of the present invention is to provide a substance which has a higher melanogenesis-inhibiting effect and is safer than kojic acid and kojic acid esters and also provide a melanogenesis-inhibiting endermic preparation for external application which contains such a substance.

In order to attain the above-mentioned object, the present inventor widely investigated kojic acid derivatives which have a further strong melanogenesis-inhibiting effect and, as a result, has newly-synthesized 2-ethoxymethyl-5-hydroxy-γ-pyrone, which is an ethyl ether of kojic acid, and has found that the new compound has an extremely high tyrosinase activity-inhibiting effect and has an effect of whitening B16 cells. Based on such findings, the inventor has hereby achieved the present invention.

Specifically, the present invention provides 2-ethoxymethyl-5-hydroxy-γ-pyrone and a melanogensis-inhibiting endermic preparation for external application containing the same compound.

DESCRIPTION OF THE PREFERRED EMBODIMENTS

2-Ethoxymethyl-5-hydroxy-γ-pyrone of the present invention is a novel compound which has not been mentioned in any of literature, publications or reports. It is a white flaky crystalline substance having a molecular weight of 170.17 and a melting point of from 71.6 to 72.0° C.

The endermic preparation for external application of the present invention can be obtained by a conventional method for preparing an emulsion, lotion, liniment, ointment or the like, wherein 2-ethoxymethyl-5-hydroxy-γ-pyrone as an active ingredient is employed with conventional bases and additives used for such preparations.

In the endermic preparation of the present invention, the amount of the above-mentioned active substance which is contained in the preparation is from 0.001 to 20% by weight, preferably from 0.01 to 10% by weight, of the total weight of the preparation.

2-Ethoxymethyl-5-hydroxy-γ-pyrone of the present invention can be produced by the following method.

PRODUCTION EXAMPLE 60 ml of water was put in a 100 ml-Erlenmeyer flask, and 10.07 g (0.24 mol) of lithium hydroxide monohydrate and then 11.37 g (0.08 mol) of kojic acid were added thereto and dissolved with stirring. While the temperature of the resulting solution was kept at 40 to 45° C., 14.80 g (0.096 mol) of diethyl sulfate was dropwise added thereto over a period of 20 minutes. Afterwards, the whole was stirred for a further 30 minutes at the same temperature and then overnight at room temperature. The pH of the reaction mixture was adjusted to 6.0 by 1N hydrochloric acid. Water was removed from the reaction mixture using an evaporator by distillation under reduced pressure, and the remaining reddish brown viscous liquid was extracted three times each with 70 ml of a hot benzene. The resulting extract was dewatered by adding anhydrous magnesium sulfate thereto, and then filtered. Benzene was removed from the resulting filtrate using an evaporator by distillation under reduced pressure. The remaining yellowish brown viscous liquid was cooled to solidify (Crude yield: 3.67 g (27%), m.p. 68 to 70° C.). The yellowish brown solid was recrystallized three times from di-isopropyl ether using active carbons to obtain a pure white crystal of 2-ethoxymethyl-5-hydroxy-γ-pyrone.

The compound is soluble in water, ethanol, methanol, chloroform, ethyl acetate and benzene but is insoluble in n-hexane.

The crystal form of the compound is a white flaky crystal (as recrystallized from di-isopropyl ether).

Figure 1:
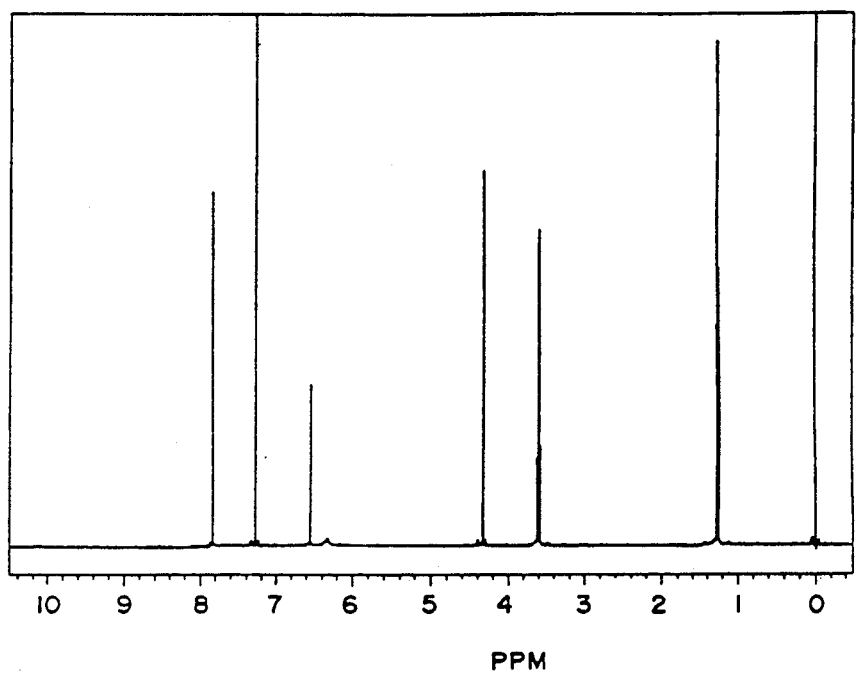
FIG. 1 shows an NMR-spectrum (solvent: CDCl$_3$) of 2-ethoxymethyl-5-hydroxy-γ-pyrone, of the compound of the present invention.
Figure 2:
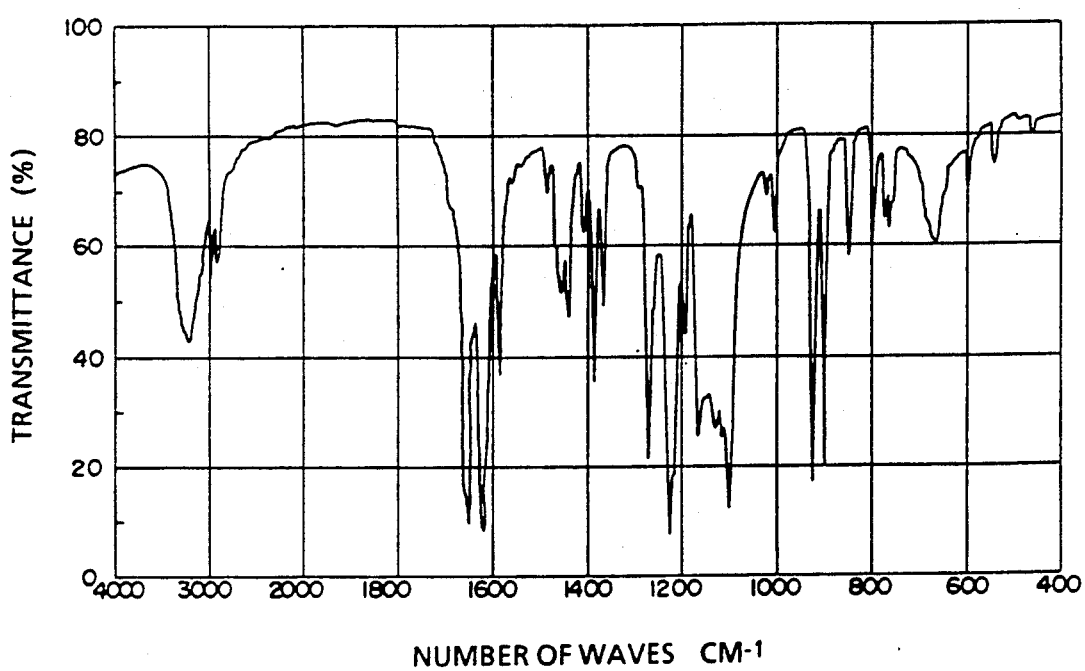
FIG. 2 shows an IR spectrum (KBr method) of the compound.
Figure 3:
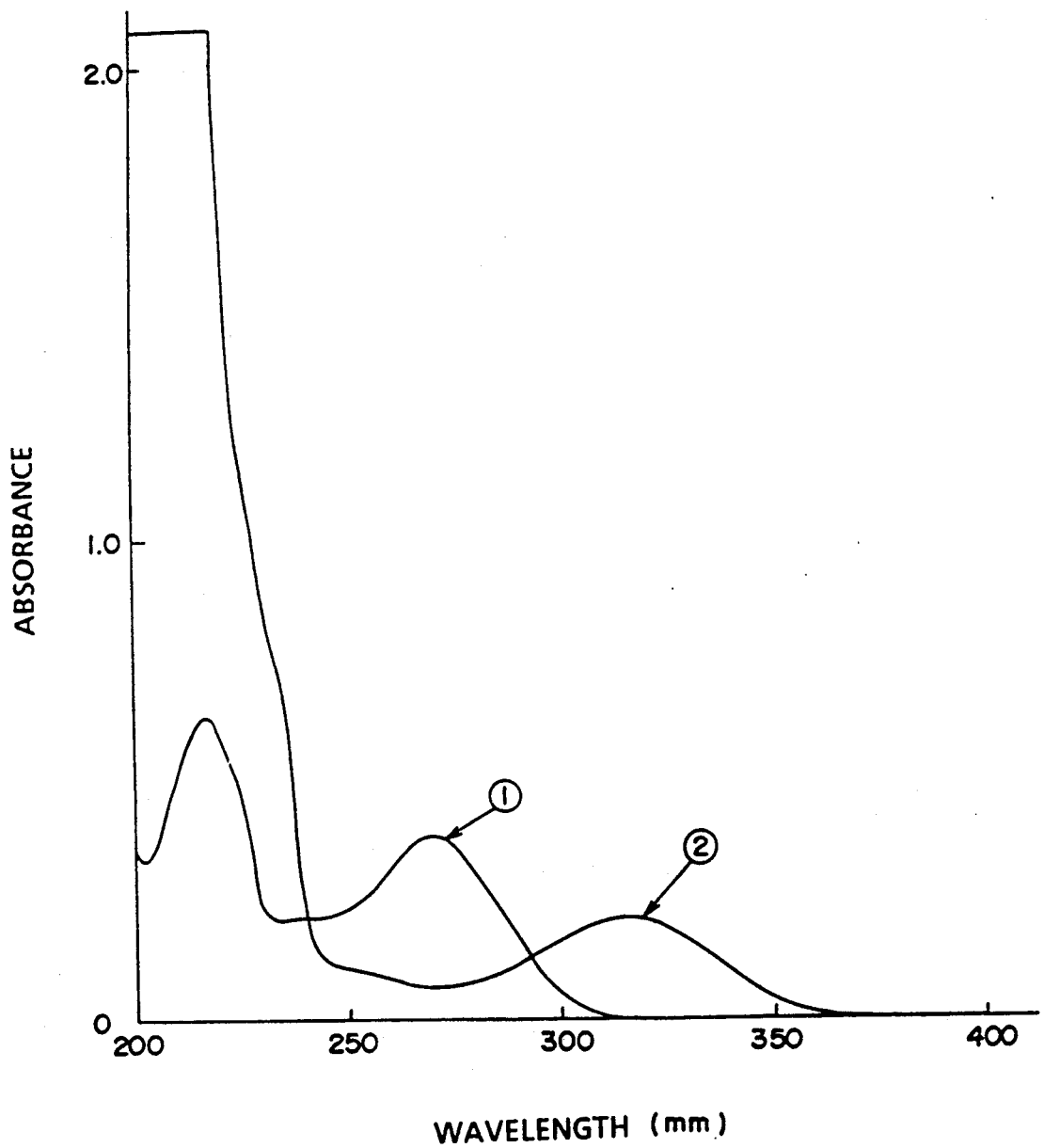
FIG. 3 shows UV spectra of the compound, wherein solvent ① is water and solvent ② is a 0.1N aqueous NaOH solution.

NMR spectrum, IR spectrum and UV spectra of the compound are shown in FIG. 1, FIG. 2 and FIG. 3, respectively.

Ferric chloride reaction of the compound is positive to show a reddish violet color (positive) reaction.

Next, some experimental examples showing the melanogenesis-inhibiting effect of the endermic preparation of the present invention will be mentioned below.

EXPERIMENTAL EXAMPLE 1:

Tyrosinase Activity Inhibition Test

A supernatant of 30,000G of mouse melanoma-derived B16 cells (hereinafter referred to as "B16 cells") was used as a tyrosinase liquid. As a buffer was used 0.1M phosphate buffer (pH 6.8). The tyrosinase-inhibiting effect of the compound of the invention was measured by the following method.

The above-mentioned tyrosinase liquid and buffer and a buffer containing 2-ethoxymethyl-5-hydroxy-$\gamma$-pyrone of a determined concentration were put in a reactor.

After 2 minutes, L-DOPA (as dissolved in a buffer) was added to the reactor whereupon the time-dependent variation of the absorbance ($\Delta$OD, 475 nm) at 37° C. was spotted.

For comparison, a kojic acid solution was tested in the same manner to determine the time-dependent variation of the absorbance under the same condition.

The results obtained are shown in Table 1.

TABLE 1

| Compound Tested | Concentration (mM) | $\Delta$475 nm/ 10 min. | Inhibition (%) |
|---|---|---|---|
| 2-Ethoxymethyl-5-hydroxy-$\gamma$-pyrone | 0.2 | 0.031 | 79 |
|  | 0.1 | 0.062 | 58 |
| Kojic Acid | 0.2 | 0.050 | 66 |
|  | 0.1 | 0.080 | 46 |
| Control | 0 | 0.147 | 0 |

As is obvious from the above-mentioned results, 2-ethoxymethyl-5-hydroxy-$\gamma$-pyrone of the present invention showed 1.5 times greater tyrosinase-inhibiting effect than the kojic acid as a control.

EXPERIMENTAL EXAMPLE 2

B16 Cells whitening Test

2-Ethoxymethyl-5-hydroxy-$\gamma$-pyrone was added to an Eagle MEM medium containing fetal calf serum in a final concentration of 0.63 mM or 0.31 mM. For comparison, kojic acid was added to the same in a final concentration of 2.5 mM or 1.25 mM. $1 \times 10^5$ B16 cells were inoculated to the culture medium. After 4 days, the medium was exchanged by a fresh one. After 5 days, cell pellets were formed, and the whitened degree of the cells was observed with the naked eye.

The results obtained are shown in Table 2 below.

TABLE 2

| Compound Tested | Concentration (mM) | Whitened Degree of Cells |
|---|---|---|
| 2-Ethoxymethyl-5-hydroxy-$\gamma$-pyrone | 0.63 | 3+ |
|  | 0.31 | 2+ |
| Kojic Acid | 2.5 | 3+ |
|  | 1.25 | 2+ |

Criteria of evaluation of whitened degree of cells:
3+: Gray, 2+: Gray to black

As is obvious from the above-mentioned results, 2-ethoxymethyl-5-hydroxy-$\gamma$-pyrone of the invention showed the same cell-whitening capacity as the comparative kojic acid as a control when the concentration of the former is ¼ of the latter.

Next, examples of the melanogenesis-inhibiting preparation of the present invention will be mentioned below, which, however, are not intended to restrict the scope of the present invention.

EXAMPLE 1

| <Milky lotion> | (parts by weight) |
|---|---|
| A. Polyoxyethylene Glycol (40 E.O.) Monostearate | 2.00 |
| Self-emulsifying Glycerin Monostearate | 5.00 |
| Stearic Acid | 5.00 |
| Behenyl Alcohol | 1.00 |
| Liquid Paraffin | 1.00 |
| Glycerin Trioctanoate | 10.00 |
| Antiseptic | ad lib |
| Perfume | ad lib |
| B. 1,3-Butylene Glycol | 5.00 |
| 2-Ethoxymethyl-5-hydroxy-$\gamma$-pyrone | 0.50 |
| Pure Water | balance |

The components of (A) were dissolved with heating to give an oily phase. Separately, the components of (B) were also dissolved with heating to give an aqueous phase.

The aqueous phase was added to the oily phase, emulsified and then cooled to obtain a milky lotion.

EXAMPLE 2

| <Lotion> | (parts by weight) |
|---|---|
| A. Polyoxyethylene (60 E.O.)-hardened Castor Oil | 1.00 |
| Ethanol | 15.00 |
| Citric Acid | 0.10 |
| Sodium Citrate | 0.30 |
| 1,3-Butylene Glycol | 4.00 |
| 2-Ethoxymethyl-5-hydroxy-$\gamma$-pyrone | 0.50 |
| Antiseptic | ad lib |
| Perfume | ad lib |
| Pure Water | balance |

The above-mentioned components were uniformly stirred, mixed and dissolved to obtain a lotion.

EXAMPLE 3

| <Emulsion> | (parts by weight) |
|---|---|
| A. Polyoxyethylene (20 E.O.) Behenyl Ether | 0.50 |
| Polyoxyethylene (60 E.O.)-sorbitol Tetraoleate | 1.00 |
| Oleophilic Glycerin Monostearate | 1.00 |
| Stearic Acid | 0.50 |
| Behenyl Alcohol | 0.50 |
| Avocado Oil | 1.00 |
| Antiseptic | ad lib |
| Perfume | ad lib |
| B. 1,3-butylene Glycol | 5.00 |
| Carboxyvinyl Polymer | 0.10 |
| 2-Ethoxymethyl-5-hydroxy-$\gamma$-pyrone | 0.10 |
| Pure Water | balance |

The components of A were dissolved with heating to give an oily phase. Separately, the components of B were dissolved with heating to give an aqueous phase.

The aqueous phase was added to the oily phase, stirred, emulsified and then cooled to obtain an emulsion.

EXAMPLE 4

| <Ointment> | (parts by weight) |
|---|---|
| A. Polyoxyethylene (60 E.O.)-sorbitol Monostearate | 1.00 |
| Polyoxyethylene (60 E.O.)-sorbitol Tetraoleate | 1.50 |
| Self-emulsifying Glycerin Monostearate | 1.50 |
| Bleached Bees Wax | 2.00 |
| Paraffin | 2.00 |
| Stearic Acid | 3.00 |
| Behenyl Alcohol | 3.00 |
| Liquid Paraffin | 5.00 |
| Antiseptic | ad lib |
| Perfume | ad lib |
| B. 1,3-Butylene Glycol | 5.00 |
| Citric Acid | 0.30 |
| 2-Ethoxymethyl-5-hydroxy-γ-pyrone | 1.00 |
| Pure Water | ad lib |

The components of (A) were dissolved with heating to give an oily phase. Separately, the components of (B) were dissolved with heating to give an aqueous phase.

The aqueous phase was added to the oily phase, stirred, emulsified and then cooled to give an ointment.

EXAMPLE 5

| <Cataplasm> | (parts by weight) |
|---|---|
| A. Polyacrylic Acid | 30.00 |
| 2-Ethoxymethyl-5-hydroxy-γ-pyrone | 10.00 |
| Sorbitan Monooleate | 1.00 |
| Pure Water | 30.70 |
| B. Sodium Polyacrylate | 7.00 |
| Aluminium Chloride | 0.30 |
| Concentrated Glycerin | 20.00 |
| Titanium Oxide | 1.00 |

The components of (A) were dissolved with heating Separately, the components of (B) were also dissolved with heating. The molten (B) was added to the molten (A), stirred and mixed to obtain a cataplasm.

As explained in detail above, the present invention provides a novel compound noticeably inhibiting formation of melanin. An endermic preparation for external application which contains the new compound is almost non-toxic and is an extremely useful melanogenesis-inhibiting endermic preparation capable of inhibiting formation of melanin.

While the invention has been described in detail and with reference to specific embodiments thereof, it will be apparent to one skilled in the art that various changes and modifications can be made therein without departing from the spirit and scope thereof.

What is claimed is:

1. 2-Ethoxymethyl-5-hydroxy-γ-pyrone.

2. A melanogenesis-inhibiting endermic preparation for external application to skin comprising 2-ethoxymethyl-5-hydroxy-γ-pyrone as an active ingredient.

3. A melanogenesis-inhibiting endermic preparation for external application as in claim 2, wherein the active ingredient 2-ethoxymethyl-5-hydroxy-γ-pyrone is present in an amount ranging from 0.001 to 20% by weight based on the total weight of the preparation.

4. A melanogenesis-inhibiting endermic preparation for external application as in claim 3, wherein the active ingredient 2-ethoxymethyl-5-hydroxy-γ-pyrone is present in an amount ranging from 0.01 to 10% by weight based on the total weight of the preparation.

5. A melanogenesis-inhibiting endermic preparation for external application as in claim 2, in a form selected from the group consisting of a lotion, an emulsion, an ointment and a cataplasm to be applied to human skin.

6. A melanogenesis-inhibiting endermic preparation for external application as in claim 5, wherein said lotion is a milky lotion.

* * * * *